Jan. 16, 1962 W. E. LAMMERTS Plant Pat. 2,121
ROSE PLANT
Filed Feb. 8, 1961
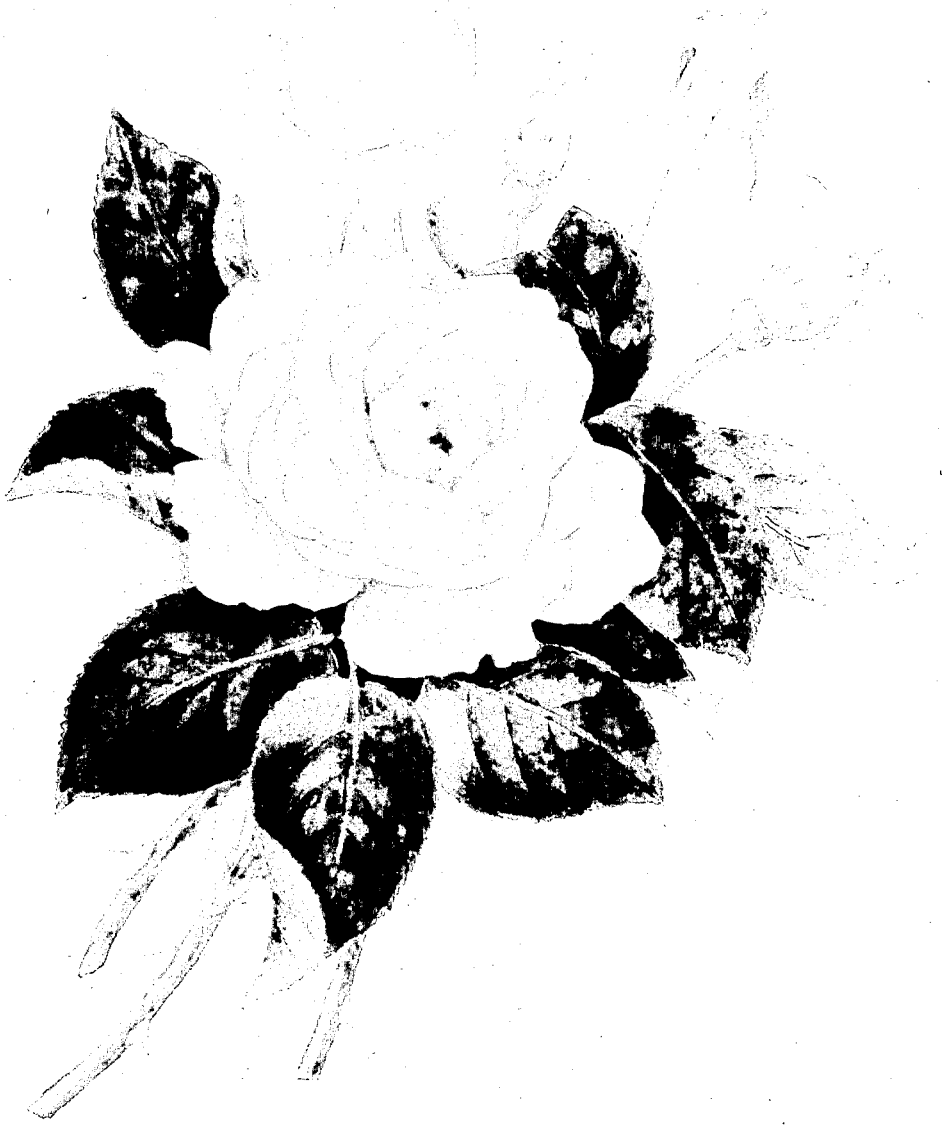
WITNESS
Addison E. Avery
INVENTOR
WALTER E. LAMMERTS
by Rummler & Snow
ATTYS.

United States Patent Office

Plant Pat. 2,121
Patented Jan. 16, 1962

2,121
ROSE PLANT

Walter E. Lammerts, Livermore, Calif., assignor, by mesne assignments, to C. R. Burr & Company, Inc., Manchester, Conn., a corporation of Connecticut Filed Feb. 8, 1961, Ser. No. 87,981
1 Claim. (Cl. 47—61)

This invention relates to rose plants and particularly concerns a new and distinctive variety of hybrid tea rose plant created by me at Livermore, California; the new variety being the result of selective breeding efforts carried on by me and under my direction, at Livermore, California, since 1954.

My new variety of rose plant originated as a seedling produced by a cross of "Queen Elizabeth" (Plant Patent No. 1,259), as the seed parent, and "Chrysler Imperial" (Plant Patent No. 1,167) as the pollen parent, the primary object of the breeding efforts being to produce a rose plant having the vigor, general garden adaptability, and glossy foliage of "Queen Elizabeth" together with the bud form, flower form and flower color of "Chrysler Imperial."

These objects have been accomplished in my new variety and successive asexual reproduction of the new plant by both budding and grafting, at Livermore, California and by shield grafting at McFarland, California has proved its novel characteristics to be fixed and to hold true to form.

The new variety is particularly distinguished from other red roses by the very bright Cherry Red color and the relative absence of magenta color in its flowers, the opened flower combining the large size of "Chrysler Imperial" with an unusually bright red color having more luster than "Chrysler Imperial." Also, the flower of the new variety has a form that is usually open cup-shaped with a more informal petal arrangement, instead of the high centered and imbricated form of "Chrysler Imperial." The bud form of the new variety is similar to that of "Chrysler Imperial," although somewhat longer-pointed, and the bud color is, at first, almost identical to that of "Chrysler Imperial." As the bud opens, however, its color lightens to a Cherry Red to Rose Red color that is brighter and more lustrous than that of "Chrysler Imperial."

The growth habit of the new variety is similar to that of "Chrysler Imperial" but is more vigorous, being intermediate between it and "Queen Elizabeth," and the abundant foliage of the new variety clothes the plant very completely, clear to the ground, so that very little of the usual thorny cane growth of most roses can be seen. The leaves of the new variety, while inheriting the glossy quality of the leaves of "Queen Elizabeth," are even larger than "Queen Elizabeth" and are larger than any other red rose. They are remarkably resistant to mildew and rust, as observed and tested at Livermore, California and at McFarland, California, and tolerate salt accumulation in hot dry areas very well. The plants, therefore, are very attractive as shrubs, even in the fall after exposure to so much water transpiration, and accumulation of salts in the leaves, that most other varieties have foliage drop or badly burn.

The accompanying illustration shows the buds, blooms and foliage of my new variety of rose plant in full color, the colors shown being substantially true, and the following is detailed description of the new variety wherein the colors have been identified according to the Horticultural Colour Chart of The British Colour Council.

*The plant*

Origin: Seedling.
Parentage:
*Seed parent.*—"Queen Elizabeth" (Pl. Pat. 1,259).
*Pollen parent.*—"Chrysler Imperial" (Pl. Pat. 1,167).
Classification: Hybrid tea rose.
Form: Bush, compact and fully clothed.
Height: 5 feet.
Growth: Vigorous, upright, and strong with heavy upright canes.
Branching: Moderate and compact.
Foliage:
*Quantity.*—Abundant.
*Number of leaves.*—5 and 7.
*Size of leaf.*—Large, compound, odd pinnate, often up to 4¾ x 6 inches in size.
*Shape, leaflet.*—Elliptic and serrated—but serrations are small for size of leaf.
*Texture.*—Smooth and glossy. Occasionally semi-glossy.
*Color.*—Upper side—Spinach Green (0960). Under side—Spinach Green (0960/3).
*Leaflets.*—Very large; 3, 5, and 7 per petiole. Size: terminal leaflet, often 2½ x 3 inches; laterals, 2 x 2½ inches.
*Petioles.*—Short length.
*Ribs and veins.*—Smooth.
*Rachis.*—Very sparse prickles.
Plant has thorns of medium size, straight or slightly hooked downward, and with a long narrow base.

*Bud*

Size: Medium, 1½ inches long, ⅞ inch diameter.
Form: Long and pointed, becoming urn shaped as bud matures. Bud opens slowly to form an open-cup-shaped flower.
Color: When sepals first divide—Rose Red (724) with some shading to Chrysanthemum Crimson (824) but mostly Rose Red. When petals begin to unfurl—Rose Red (724/1).
Sepals: Sparsely branched and hooded over the young bud. Sepals are spear-shaped and curl back as bud develops. Color: inside—Pod Green (061/2); outside—Pod Green (061) with purple red anthocyanin coloring in central portion.
Calyx: Funnel-shaped and broad.
*Size.*—Medium.
*Aspect.*—Very slightly hairy. Does not split.
Peduncle:
*Length.*—2 to 2½ inches.
*Aspect.*—Very slightly hairy.
*Strength.*—Erect and moderately heavy, exceptionally sturdy.
*Color.*—Green with purple red anthocyanin coloring on side toward sun.

*Flower*

Blooms: Continuously and profusely from spring through late fall.
Size: Very large. 4½ to 5 inches in diameter and approximately 1¼ inches in depth.
Borne: Normally single. Occasionally clustered.

Shape: Cup shaped when bloom first opens changing to open cup shape as bloom develops.

Petalage: 20 to 22 petals, informally arranged.

*Form.*—Obovate, with smooth undulating edges.

*Color.*—Outer petals.—Cherry Red (722) fading at margins to Rose Red (724); Spirea Red (025/2) at base. Inside petals—Cherry Red (722). Reverse side—Rose Red (724/1) with Solferine Purple (26) at base.

*Lasting quality.*—Petals stay on stem 10 to 15 days.

Petaloids:

*Number.*—4 to 6.

*Size.*—Approximately ⅓ to ½ the normal petal size.

*Color.*—Same as petals.

Texture: Soft.

Appearance: Velvety and shiny.

Fragrance: Moderate.

Discoloration: After full bloom petals fade and eventually brown.

Weather effect: Flower fades to light Rose Red (724/2) in hot weather.

Persistence: Tends to hang on and dry.

Lasting quality: 3 days, on plant and as cut flower.

Disease resistance: Resistant to mildew and rust, as observed at Livermore, Calif. and at McFarland, Calif.

*Genital organs*

Stamens:

*Anthers.*—Length—3/32 inch. Arrangement—regular. Number—approximately 120 to 125.

*Filaments.*—Length—3/16 to 5/16 inch. Color—Carmine (21/1).

Pollen: Color—Yellow Ochre (07).

Pistils:

*Number.*—92 to 97.

*Length of style.*—Approx. ¼ to ⅜ inch.

*Stigmas.*—Color—Naples Yellow (403/3).

Ovaries: Inferior.

*Fruit*

Fertile, truncated ovoid in shape, and of yellow color at maturity.

With reference to the accompanying illustration, a tabulation of the principal and distinguishing colors of my new variety of rose plant, according to the British Colour Council Horticultural Colour Chart, is as follows:

| | Sheet | Color | Number |
|---|---|---|---|
| Open bloom, main area of inside surface of petals. | 157 | Cherry | 722 |
| Changing to at margins of outer petals. | 158 | Rose Red | 724 |
| Reverse side of petals | 158 | Rose Red | 724/1 |
| Bud, main color of petals | | | |
| Sepals, Outside surface (shaded to Purple Red at center) | 120 | Pod Green | 061 |
| Inside surface | 120 | Pod Green | 061/2 |
| Leaf, Upper side surface | 187 | Spinach Green | 0960 |
| Under side surface | 187 | Spinach Green | 0960/3 |

From the foregoing it will be seen that my new and distinctive variety of rose plant most nearly resembles its pollen parent, "Chrysler Imperial." The new plant, however, is particularly distinguished from its pollen parent, and all other red roses, by the brilliant Cherry Red color of its opened blooms and the relative absence of magenta coloring. A further distinction resides in the very large and abundant foliage of the new plant, which is even larger than "Queen Elizabeth," and which clothes the plant clear to the ground.

These features, combined with the large size of the flowers, the inherent resistance of the plant to damage by salt accumulation and transpiration in dry fall weather, and the sturdy compact habit of its growth, provide an unusually attractive shrub plant which retains its decorative and bloom producing quality throughout the growing season and well into the late fall.

Having now described my new variety of rose plant, I claim:

A new and distinct variety of hybrid tea rose plant, substantially as herein shown and described, characterized particularly by the very bright Cherry Red color and the relative absence of magenta color in its blooms, the large size of its blooms, its very large and glossy foliage which abundantly clothes the plant, its sturdy compact habit of growth, and its ability to tolerate salt accumulation in the leaves in hot dry areas.

No references cited.